United States Patent [19]
Arp

[11] Patent Number: 4,890,866
[45] Date of Patent: Jan. 2, 1990

[54] TUBING CONNECTOR

[75] Inventor: Robert A. Arp, Eden Prairie, Minn.

[73] Assignee: Mentor Corporation, Minneapolis, Minn.

[21] Appl. No.: 323,343

[22] Filed: Mar. 14, 1989

[51] Int. Cl.[4] ............................................. F16L 33/22
[52] U.S. Cl. .................................. 285/243; 285/157; 285/179; 285/319; 285/331; 285/423
[58] Field of Search ............... 285/243, 242, 322, 319, 285/331, 157, 179, 310, 309, 423

[56] References Cited

U.S. PATENT DOCUMENTS

| 409,066 | 8/1889 | Ravenel . | |
|---|---|---|---|
| 3,476,412 | 11/1969 | Demler, Sr. | 285/322 |
| 3,695,632 | 10/1972 | Kruse et al. . | |
| 3,833,246 | 9/1974 | Wake . | |
| 3,868,130 | 2/1975 | Schwertner et al. . | |
| 3,885,819 | 5/1975 | Egrer et al. . | |
| 3,997,195 | 12/1976 | Bartholomew | 285/331 X |
| 4,238,132 | 12/1980 | Palmaer . | |
| 4,288,112 | 9/1981 | Stoll | 285/322 X |
| 4,313,628 | 2/1982 | Duenke . | |
| 4,321,911 | 3/1982 | Offutt . | |
| 4,343,498 | 8/1982 | Campanini . | |
| 4,440,425 | 4/1984 | Pate et al. | 285/322 X |
| 4,451,070 | 5/1984 | Sauer . | |
| 4,537,183 | 8/1985 | Fogarty . | |
| 4,632,435 | 12/1986 | Polyak . | |
| 4,632,437 | 12/1986 | Robson et al. | 285/243 X |
| 4,673,199 | 6/1987 | Renfrew | 285/319 X |

FOREIGN PATENT DOCUMENTS 31409  7/1981  European Pat. Off. ............ 285/322

Primary Examiner—Thomas F. Callaghan
Attorney, Agent, or Firm—Plante Strauss Vanderburgh

[57] ABSTRACT

There is disclosed a connector for attachment of flexible plastic tubing which is most compatible with filament reinforced tubing which resists elastic expansion. The connector has a central radial flange with opposite cylindrical ends which provide mandrels to receive adjacent ends of tubing. A cylindrical cage surrounds the cylindrical ends and supports chuck members. A pair of collet members are provided which slide over the tubing and the chuck members, compressing the chuck members radially inwardly without axial movement of the chuck members relative to the tubing. This deflects the chuck members into the wall of the tubing, thereby locking the tubing securely onto the mandrel. The collet member has an internal annular groove on its inside wall which receives an outer edge of the chuck members, thereby serving as a detent or interlock to resist the retraction of the collet member once it is moved into final position.

27 Claims, 4 Drawing Sheets

TUBING CONNECTOR

BACKGROUND OF THE INVENTION

1. Field of Invention

This invention relates to a tubing connector and, in particular, to a connector useful for plastic tubing, particularly medical tubing.

2. Brief Statement of the Prior Art

Connectors for plastic and rubber tubing have been devised for a multiplicity of purposes and applications. In surgically implanted prosthetic devices, connectors are frequently used. These connectors have ranged in complexity from simple suture ties to secure tubing onto a mandrel to sophisticated mechanical fasteners which may require special tools for assembly.

Examples of connectors used for surgical implants can be found in U.S. Pat. Nos. 4,537,183 and 4,632,435. These connectors are intended to be used with highly elastic and compressible silicone tubing such as used within the fluid system of a prosthetic device such as an implantable penile prosthesis.

When tubing is part of a prosthetic device, it is desirable that it have a long life with little or no necessity for service and maintenance. A preferred tubing is reinforced silicon which incorporates a helical wound Nylon filament reinforcement, to resist kinking. This tubing is typically composed of two extruded layers of silicone with the helical wound filament confined between them. Although the bond retention between these two layers is quite substantial, a highly localized shear force will separate these layers and damage the tubing.

The tubing connectors of both the aforementioned patents have compression fingers which initially exert radial compression on the tubing and then are driven axially into their final position. Although the fingers on these connectors their final position. Although the fingers on these connectors are rounded to minimize tubing damage, the combination of radial pressure and axial loading can tear the outer silicone layer, initiating separation and loss of tubing integrity.

When a connection is made on a prosthetic device, the surgeon should be provided with visual assurance that the connector is being assembled properly. With one of the aforementioned connectors, it is required to insert the tubing into a blind recess or pocket before engaging the locking member. With no visual indication that the tubing is fully seated, the surgeon can only assume that a secure connection will result.

During the surgical implant procedure, the tubing is temporarily attached on the connector to determine if the proper amount of fluid has been charged to the system and also to test the device for operation under fluid pressure. With both the aforementioned connectors, the surgeon has difficulty with this process. With one connector design, the tubing must be severely expanded as it is forced onto a large tapered mandrel, whereas the other connector design uses a small mandrel of very short proportion, offering minimal tubing retention. For this preassembly, it would be advantageous if the tubing could be assembled and disassembled onto the connector in a facile manner and also retain itself under modest internal fluid pressure for test purposes.

It is sometimes found that a completed connector must be disassembled to make further adjustment to the prosthetic device. These problems usually occur late in the procedure when the surgeon feels most pressured for time. The aforementioned connectors offer no consideration for effective removal and if forcibly dislodged, tubing and connector damage usually results. This places severe restrictions on the surgical procedure as all or part of the prosthetic device may have to be replaced or the surgeon may be forced to compromise a good installation.

Surgeons often prefer to handle and secure the connector with their fingers. This gives them better control over the assembly and provides a sense of feel when the locking members have been finally engaged. The connectors of the aforementioned patents can only be assembled by the application of considerable force, and a connector tool is typically used to drive the end clamps of these connectors into their final positions. These tools preclude determining that the clamps have been finally seated by a sense of feel.

Another difficulty is that the prior tubing connectors for prosthetic devices have external fissures or grooves in which body tissue tends to grow, complicating the removal of the prosthetic device.

OBJECTIVES OF THIS INVENTION

It is an object of this invention to provide a tubing connector useful with flexible plastic tubing.

It is an also an object of this invention to provide a tubing connector useful with reinforced silicone tubing.

It is another object of this invention to provide a tubing connector in which the ends of tubing that are assembled to a connector body are visibly seated before the locking members are engaged.

It is another object of this invention to provide a tubing connector in which the ends of tubing which are secured within the connector are not subjected to extreme axial shear, upon closure of the connector locking members.

It is another object of this invention to provide a tubing connector which has sufficient retention for the ends of the tubing to permit testing of the prosthetic device prior to the engagement of the connector locking members.

It is another object of this invention to provide a tubing connector which can be simply disassembled without damaging the tubing or the connector.

It is another object of this invention to provide a tubing connector which presents a smooth external surface and thereby provides minimal opportunity for in growth of body tissue.

It is another object of this invention to provide a tubing connector which can be assembled with one's fingers, without requiring special assembly tools.

It is another object of this invention to provide the aforementioned tubing connector as a component of a medical prosthetic device.

It is another object of this invention to provide the aforementioned tubing connector to connect the ends of tubing for the fluid system of an implantable prosthetic device.

It is another object of this invention to provide the aforementioned tubing connector to connect the ends of tubing for the fluid system of a penile implant.

BRIEF DESCRIPTION OF THE INVENTION

This invention comprises a connector and fittings for attachment of flexible plastic tubing, and also a connector most compatible with filament reinforced tubing which resists elastic expansion. The connector has a central radial flange with opposite cylindrical ends which provide mandrels that receive the adjacent ends of tubing. A cylindrical cage surrounds the cylindrical ends and supports chuck members. A pair of collet members are provided which slide over the tubing and the chuck members, compressing the chuck members radially inwardly into the wall of the tubing, thereby locking the tubing securely onto the mandrel. The collet member has an internal annular groove on its inside wall which receives an outer edge of the chuck members, thereby serving as a detent or interlock to resist the retraction of the collet member once it is moved into final position.

The invention provides the advantages of a smooth external surface which will resist ingrowth of tissue. Additionally, the external corners of the connector are rounded with no sharp edges. The ends of the tubing can be assembled onto the tubing connector and the prosthetic device can be pressurized with fluid prior to final assembly so that the surgeon can perform an intermediate check of the prosthetic device before the collet members are moved into their closed positions. Apertures are provided in the outer cage of the connector body to permit the surgeon to observe that the ends of the tubing are completely inserted over the mandrels and abutted against the radial flange of the connector body. The entire connector can be assembled and disassembled by hand, without any tools and without damaging the tubing, or the connector.

The connector is ideally suited for reinforced filament plastic tubing as the chuck members exert radial compression only with no axial shear which could damage the tubing. The connector can be used to connect two ends of tubing, or can be used as a part of a fitting for the attachment of tubing to a prosthetic device.

BRIEF DESCRIPTION OF THE DRAWINGS

The invention will be described with reference to the FIGURES of which.

DESCRIPTION OF THE PREFERRED EMBODIMENT

Figure 1:
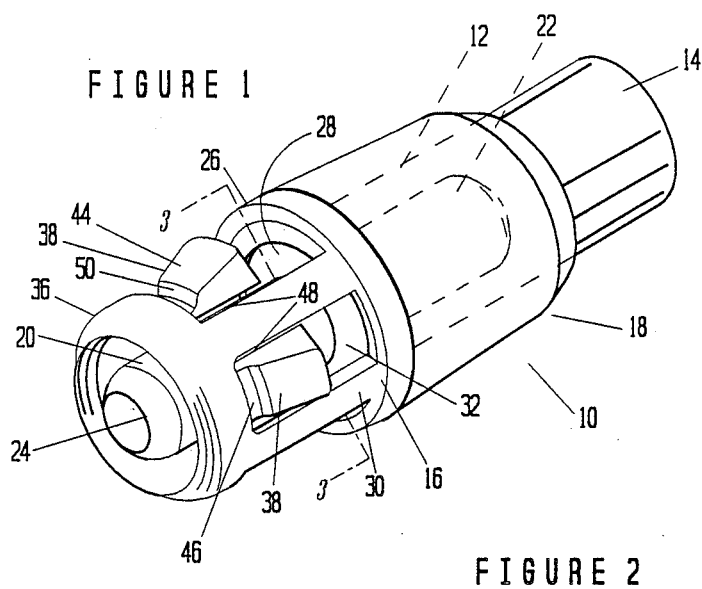
FIG. 1 is a perspective view of a partially assembled in line connector and tubing.

Referring now to FIG. 1, a tubing joint 10 is shown in partial assembly with an end 12 of tubing 14 secured to one end of the tubing connector 16 and with the collet member 18 moved into its final, locking position on the connector. The tubing connector has a pair of cylindrical mandrels 20 and 22 which have entirely smooth cylindrical outer surfaces. Preferably, the mandrels have radiuses distal edges 24. Each mandrel projects from opposite faces of a central radial flange 26 which, preferably, has an undercut 28 on each of its opposite faces to provide a stop for the ends of the tubing, as described hereinafter.

A tubular cage 30 projects axially from the radial flange 26 and extends substantially the entire length of each 15 mandrel, terminating preferably a short distance short of the length of the mandrel. The cage 30 has a plurality of through apertures such as 32 which are positioned at equal angular increments; four surround each mandrel in the preferred embodiment. The through apertures 32 are interspaced by unbroken longitudinal ribs 34 which terminate in annular end rings such as 36.

A plurality of chuck members 38 are integrally formed with each end ring 36, projecting inwardly from its inside face 40, so that a chuck member 38 is located within each of the through apertures. The chuck members 38 have inside, arcuately concave faces of the same diameter as the internal diameter of the tubular cage 30 and have a length which extends substantially, but not entirely, the length of the through apertures 32, thereby providing open windows 42 immediately adjacent the radial flange 26. The chuck members 38 are wedge shaped, with an inclined cam surface 44 that tapers upwardly along an inwardly axial direction. The chuck members 38 are secured to the end rings with integral hinges 46 that are formed by axial slots 48 between the longitudinal ribs 34 and the chuck members 38. To improve flexibility of the hinges 46, annular grooves 50 are formed about the forward ends 52 of the chuck members 38, thereby reducing the thickness of the connecting web between the chuck members 38 and the rings 36 and 37.

Figure 2:
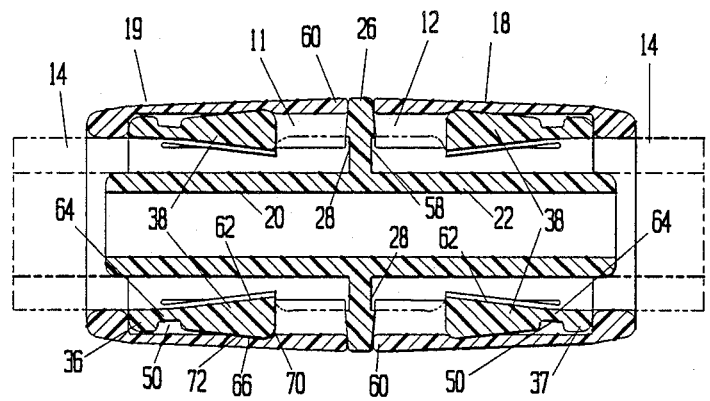
FIG. 2 is a sectional view of an assembled tubing joint with the tubing connector shown in FIG. 1.

Referring now to FIG. 2, there is illustrated a sectional view through an assembled connector. As there illustrated, opposite and opposed ends 11 and 12 of tubing 14 are seated on cylindrical mandrels 20 and 22 of a symmetrical connector body 16. The tubing ends 11 and 12 abut against the opposite faces 56 and 58 of the radial flange 26, which has a shallow undercut 28 on each face to receive the ends of the tubing. The collet members 18 and 19 are shown in their interlocking positions. In these positions, the collet members 18 and 19 abut at their medial ends 60 to provide a smooth continuous external surface to the completed tubing joint.

The chuck members 38 are displaced radially inwardly, exerting a radial compression on the tubing 14 which deforms, as illustrated, with the inside arcuate undersurface 62 of these chuck members 38 firmly embedded into the tubing. As previously mentioned, the annular grooves 50 about the distal ends of the chuck members 38 provide webs 64 of reduced thickness between the end rings 36 and the chuck members 38, thereby serving as a flexible hinge, permitting the inward deflection of the chuck members as the collet members are advanced over the chuck members.

As previously mentioned, each collet member has an annular groove 66 on its inside surface 68 that provides an interlock to prevent the dislodgement of the collet member once it is seated in its interlocking position illustrated in FIG. 2. This annular groove preferably has an inclined, medial wall 70 that resists but does not completely prevent removal of the collet member. Preferably, the angle of inclination of this medial wall 70 is from 20 to about 30 degrees to the longitudinal axis of the collet member. The lateral wall 72 of the annular groove preferably has an inclination which corresponds to the inclination of the cam surface 44 of the chuck members 38, thereby providing a bearing surface between the collet member and the chuck members.

Figure 3:
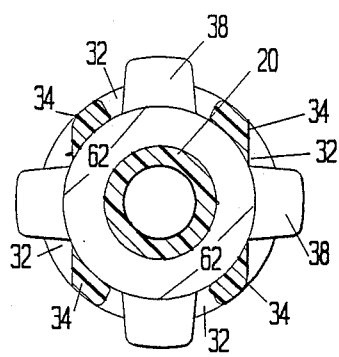
FIG. 3 is a sectional view along the line 3-3' of FIG. 1.
Figure 4:
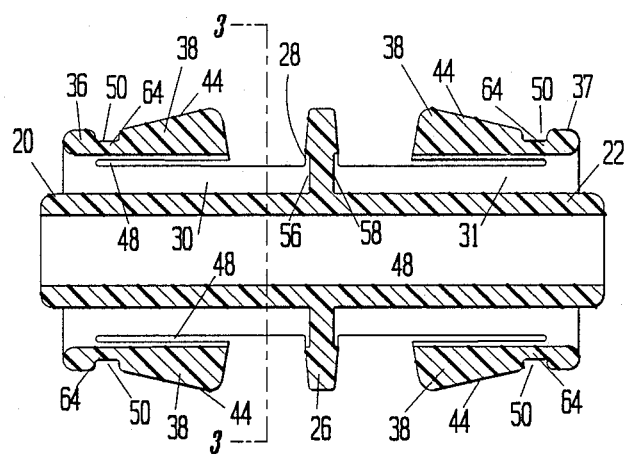
FIG. 4 is an elevational sectional view of the in line connector body of the invention.

Referring now to FIGS. 3 and 4, the connector body is illustrated in sectional views. As previously mentioned, the connector body has cylindrical mandrels 20 and 22 having smooth, unbroken and continuous outer cylindrical surfaces. Preferably, the tubing connector is employed for connection of opposite ends of tubing and, for this purpose, the connector body is symmetrical with identically shaped mandrels 20 and 22 projecting in opposite directions from a central, radial flange 26. Preferably the cylindrical mandrels 20 and 22 have a length which is from 1.5 to 5 times their outside diameter, and most preferably, from 2 to about 3 times their outside diameter. This provides sufficient frictional retention of the tubing on the mandrels to permit pressure testing of the assembly without closing of the locking collet members.

The radial flange 26, as previously mentioned, has a shallow undercut 28 on each of its opposite faces 56 and 58, thereby serving as a receptacle and stop for the ends of the plastic tubing. Each of the mandrels are surrounded by a tubular cage 30 and 31 which project laterally in opposite directions from the central radial flange 26 and terminate in annular end ring 36 and 37 that entirely surrounds the distal ends of its respective mandrel.

The tubular cages 30 and 31 have a plurality of through apertures 32, preferably four which are located at equal angular spacings about the periphery of each cage, thereby forming continuous, longitudinal ribs 34 which extend between the central radial flange 26 and each of the end rings 36 and 37. The chuck members 38 are integral with the end rings and project therefrom into the open spaces of the through apertures 32, interconnected to their respective end ring 36 and 37 by webs 64 of reduced thicknesses formed by the annular grooves 50. The undersurface 62 of the chuck members are arcuately concave as shown in FIG. 3, and have the same diameter as the inner diameter of the cage. The chuck members 38 are separated from the longitudinal ribs 34 of each cage 30 by the axial slots 48 that extend to the end rings 36 and 37.

Figure 5:
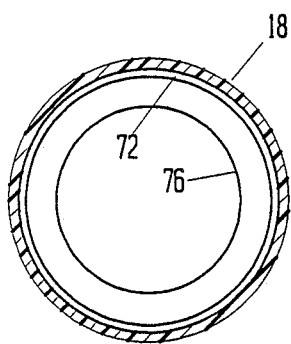
FIG. 5 is a view along the line 5-5' of FIG. 6.
Figure 6:
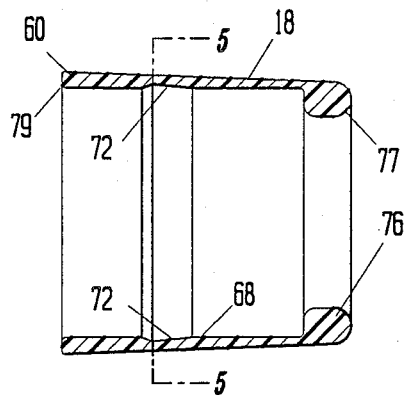
FIG. 6 is a sectional view of the collet member used in the invention.

Referring now to FIGS. 5 and 6, the collet members 18 will be described. As apparent from FIG. 2, two collet members 18 and 19 are provided with each tubing connector body 54. These collet members are placed over the mating ends 11 and 12 of tubing 14 and are freely slidable thereover, having an internal diameter at their outer ends 76 which closely conforms to the outside diameter of the tubing 14, thereby avoiding any gaps between the tubing 14 and the ends 76 of the collet members 18 that would permit ingrowth of tissue. The inside diameters of the medial ends 60 of the collet members 18 are slightly greater than the outer diameter of the end rings 36 and 37 to permit the collet members 18 to be slid over the connector body 16.

In assembly of the tubing joint, the ends of the tubing are slid over the opposite mandrels 20 and 22 until the ends of the tubing are abutted against the opposite undercut faces 56 and 58 of the radial flange 26. In this position, the frictional engagement of the tubing 14 to the connector body 16 will be sufficient to permit the surgeon to apply a slight, operative internal pressure to the prosthetic device, thereby determining whether the device has the proper quantity of fluid. If fluid needs to be added or removed from the prosthetic device, the surgeon can readily disassemble the tubing joint by removing an end of the tubing from its mandrel. Once the surgeon is satisfied that the prosthetic device contains the proper quantity of liquid, the collet members 18 are slid over the connector body 16, compressing the chuck members 38 inwardly into the side wall of the tubing. The chuck members 38 are compressed as the medial ends 60 of the collet members 18 advance over the outer, inclined ramp or cam surfaces 44 of the chuck members 38. Once the collet members 18 have been advanced to their interlocking positions with their medial ends 60 seated against the radial flange 26, the annular grooves 66 on their inside surfaces are positioned opposite the walls 44 of the chuck members 38. The chuck members 38 expand radially outwardly an incremental amount, thereby interlocking the collet member 18 in the assembly and serving as a positive detent that resists the removal of the collet members 18.

Figure 8:
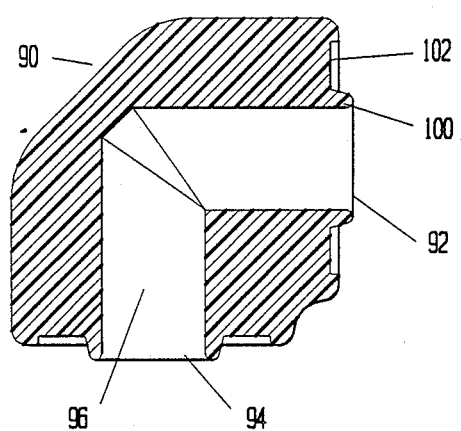
FIG. 8 is a sectional view along the line 8—8 of the right angle connector shown in FIG. 7.
Figure 7:
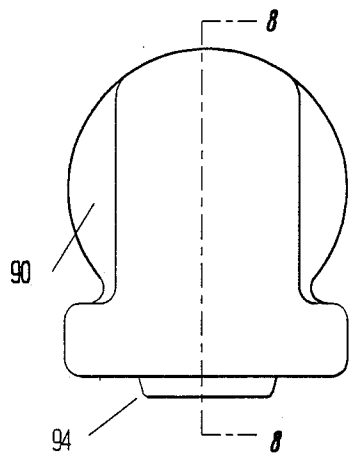
FIG. 7 is a view of a right angle embodiment of the connector of this invention.

Referring now to FIGS. 7 and 8, a right angle connector block is shown which, when combined with the tubing connector of this invention, will form angled connector fittings that are useful with the prosthetic device. FIG. 8 is a sectional view along line 8-8' of FIG. 7. The connector block comprises an elbow 90 having central bores 96 on contiguous faces 92 and 94 which intersect within the body to provide a through passageway with a 90 degree deflection. All of the external corners of the connector body are smoothly radiuses, as shown. As apparent from FIG. 8, the opposite sides 93 and 95 of the right angle connector are flat, to permit grasping of the connector body with a surgeon's hemostat while moving the connector body into its final placement.

Figure 9:
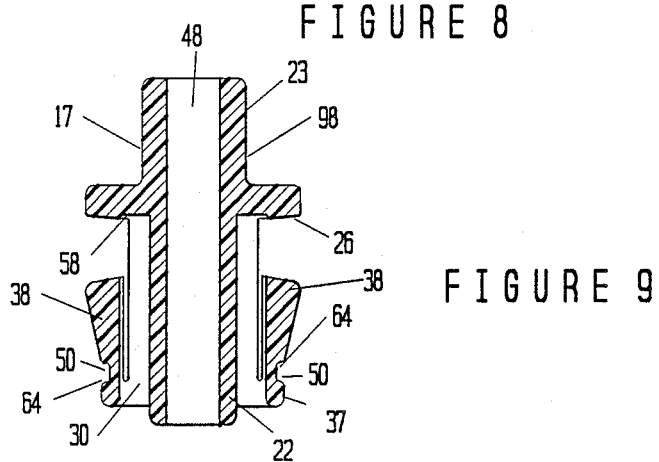
FIG. 9 is a sectional view of an embodiment of a tubing connector.

A suitable tubing connector 17 for assembly with the connector blocks 90, is shown in sectional view in FIG. 9. Connector 17 is similar to connector 16, previously described, however, the tubular cage 30 is not present on end 98 of the connector body. Instead, only a mandrel 23 of reduced length extends from the central flange 26.

Preferably each connecting face 92 and 94 of the connector block 90 has a concentric annular rib 100 which will abut the flange 26 of the connector body 17. The abutted flange and rib, in combination with the engagement of mandrel 23 into bore 96, form an assembly which is permanently bonded together by suitable means such as solvent or ultrasonic fusion. During the bonding, the annular ribs on the faces of the connector blocks will melt and flow into the recesses 102 which will entrap any excess material from this process and contain it within the bond area.

Figure 10:
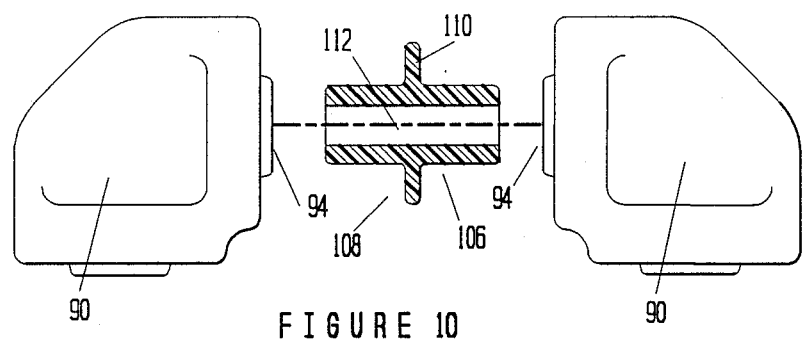
FIG. 10 is an exploded view of two of the right angle connectors of FIG. 8 with an in line bushing connector.

As shown in FIG. 10, an in line bushing 106 can be used to connect two of the connector bodies shown in FIGS. 7 and 8 to provide a 180° return fitting, which is shown assembled in FIG. 1. The bushing 106 has a centrally located radial flange with opposite faces 108 and 110 which are bonded to the opposing faces of two right angle connectors 90. The bushing has a through passageway 112.

Figure 11:
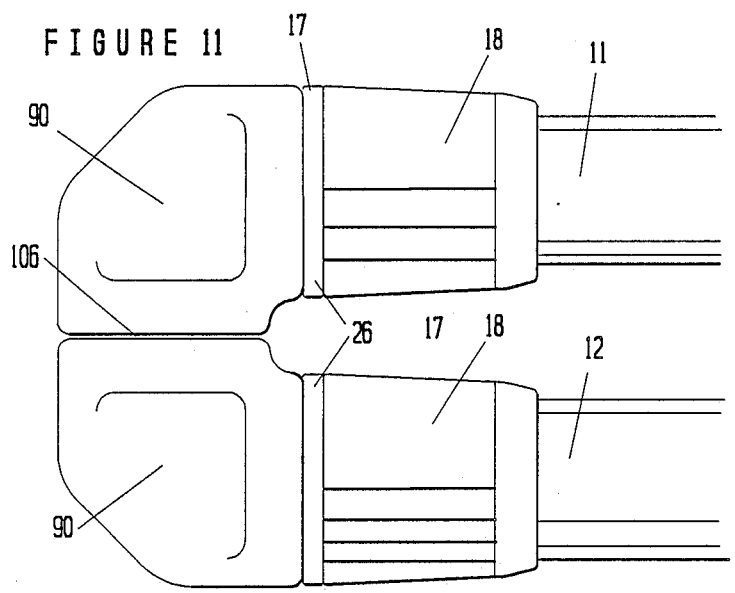
FIG. 11 illustrates an assembled 180 degree connector of the invention.

FIG. 11 shows two connector blocks 90 assembled to form a 180 degree fitting in which tubing 11 and 12 are secured with connectors 17 of the invention. The collet members 18 are shown advanced into their tube locking positions, with their ends abutting the radial flanges 26 of the tubing connectors 17. The in line bushing 106 connects between the two right angle connectors 90, as described with reference to FIG. 10.

The tubing connector is intended for use with flexible plastic tubing, including filament reinforced plastic tubing. An example of such tubing is a helical-wound, Nylon-filament, reinforced silicon tubing. This tubing has walls which can be deformed and compressed in the manner shown in FIG. 2, but which greatly resist any radial expansion as the tubing has little or no hoop stress elasticity.

The tubing connector of this invention provides a smooth, unbroken external wall which provides little or no opportunity for tissue ingrowth. The smoothly radiuses corners of the connector and collet members avoid unintentional damage and premature failure of the tubing. The connector also has open windows which permit the surgeon to visually observe that the ends of the tubing have been firmly seated against the radial flange. As the tubing is frictionally engaged on the connector mandrels, the connector permits the surgeon to test the prosthetic device under fluid pressure before the connector is secured with the collet members. This also permits facile disassembly of the tubing joint to permit removal or addition of fluid to the prosthetic device. Since the chuck members hinge from a stationary point relative to the tubing, they compress into the tubing in a radial movement only with no longitudinal movement. Thus, upon routine closure of the connector assembly, axial shear damage to the tubing is precluded.

In the event that the connector must be disconnected after final assembly, the exposed collet members can be grasped and retracted axially and the tubing removed without any damage, thus avoiding the necessity to cut the tubing for removal of the connector. Since the collet members can be seated by finger pressure alone, no special tools are required for assembly or disassembly.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

I claim:

1. A connector for flexible plastic tubing comprising:
   a. a connector body having:
      (1) a tubular mandrel with a smooth, entirely cylindrical outside wall of a diameter slightly larger than the internal diameter of said plastic tubing to provide a frictional engagement with an end of said tubing placed thereover;
      (2) a radial flange surrounding said mandrel to serve as a tubing stop;
      (3) a tubular cage integral with and extending from said radial flange, coextensive with said mandrel, and comprising a cylindrical body having an internal diameter greater than the outside diameter of said tubing with a plurality of angularly-spaced-apart apertures, and having an axial length which extends substantially the length of said mandrel;
      (4) a plurality of chuck members, one each positioned in a respective one of said apertures, and hinged to the laterally distal edge of its respective aperture, said chuck members comprising a wedge of thickness increasing axially towards said radial flange and a length less than the axial length of its respective aperture; and
   b. a collet member having:
      (1) a distal end with a diameter closely conforming to the outside diameter of said tubing to be slidably received thereover;
      (2) a medial end facing said connector body with an internal diameter permitting it to be received over said tubular cage to compress said chuck members radially inwardly and into the wall of tubing surrounding said mandrel; and
      (3) detent means on its inside wall to lock said collet member to said connector body and prevent the axial dislodgement of said collet member when placed over said connector body and end of tubing.

2. The connector of claim 1 wherein the external surface of said collet member is exposed to permit grasping and retraction for disassembly and removal of said tubing.

3. The connector of claim 1 wherein said detent means comprises an annular groove on the inside wall of said collet member, axially aligned with the distal ends of said chuck members whereby the distal edges of said chuck members are received within said groove and serve as axial locks preventing dislodgement of said collet member.

4. The connector of claim 3 wherein the distal edges of said chuck members which are received in said annular groove of said collet member are inclined whereby said collet member may be grasped and retracted axially and said inclined edges are effective to radially deflect said chuck members and permit facile disassembly of said collet member from said connector body.

5. The connector of claim 3 wherein the surface of said annular groove which receives the distal edges of said chuck members is inclined whereby said collet member may be grasped and retracted axially and said inclined surface is effective to radially deflect said chuck members and permit facile disassembly of said collet member from said connector body.

6. The tubing connector of claim 1 wherein the distal end of said collet member extends beyond the distal end of said tubing mandrel, whereby said tubing is free of expansive tension as it exits said collet member.

7. The tubing connector of claim 1 wherein the inner and outer distal edges of said collet member are full radii.

8. The connector of claim 1 wherein the exterior wall of said collet member is tapered to a reduced outer diameter at its distal end.

9. The tubing connector of claim 1 wherein the distal end of said collet member has a reduced inside diameter closely conforming to the outside diameter of said tubing.

10. The connector of claim 1 wherein said connector body is symmetrical about said radial flange to provide a pair of oppositely directed mandrels for the connection of two ends of tubing.

11. The connector of claim 10 in combination with two collet members which are received over the adjacent ends of tubing mated onto said connector body.

12. The connector of claim 11 wherein the medial ends of said two collet members abut against said radial flange and are of equal diameter therewith and collectively form a smooth axial profile.

13. The connector of claim 1 in combination with reinforced tubing of plastic having hoop stress reinforcement windings embedded within its tubing wall, and received over said mandrel.

14. The connector of claim 13 wherein said chuck members deflect into the wall of said tubing without axial movement, thereby precluding axial shear of the outer surface of said tubing wall.

15. The connector of claim 14 wherein the inner distal edges of said chuck members are essentially sharp at the point of compression into said tubing wall.

16. The connector of claim 1 wherein said chuck members are attached to the distal end of said collet members with hinge means permitting their radially inward deflection.

17. The connector of claim 16 wherein said chuck members are integral with said collet member and said hinge means comprises an integral web between said chuck members and said collet member, with a thickness reduced sufficiently to permit flexing.

18. The tubing connector of claim 1 wherein four windows and four chuck members are provided at 90 degree angular spacings.

19. The tubing connector of claim 1 wherein the medial ends of said apertures are adjacent said radial flange, thereby visually exposing the abutment of said tubing ends against said flange.

20. The tubing connector of claim 1 wherein said cylindrical outside wall of said mandrel has a length from 2 to 4 times its outside diameter, thereby providing a preselected degree of frictional engagement of tubing received over said cylindrical outside wall sufficient to retain said tubing against moderate internal pressure without assembly of said collet member.

21. The tubing connector of claim 19 wherein said cylindrical outside wall has a length from 2.25 to about 3 times its outside diameter.

22. A connector for flexible plastic tubing comprising:
a. a connector body having:
  (1) a tubular mandrel for frictionally receiving an end of said tubing placed thereover;
  (2) a radial flange surrounding said mandrel to serve as a tubing stop;
  (3) a tubular cage integral with and extending from said radial flange, coextensive with said mandrel, and comprising a cylindrical body having an internal diameter greater than the outside diameter of said tubing;
  (4) a plurality of chuck members hinged to the laterally distal edge of said tubular cage, said chuck members comprising wedges of thickness increasing axially towards said radial flange; and
b. a collet member having:
  (1) a distal end with a diameter closely conforming to the outside diameter of said tubing and slidably received thereover;
  (2) a medial end facing said connector body with an internal diameter permitting it to be received over said tubular cage to compress said chuck members radially inwardly without axial movement of said chuck members, and into the wall of tubing surrounding said mandrel.

23. The connector of claim 22 in combination with reinforced tubing of plastic having hoop stress reinforcement windings embedded within its tubing wall, and received over said mandrel.

24. The connector of claim 23 wherein the inner distal edges of said chuck members are essentially sharp at the point of compression into said tubing wall.

25. The connector of claim 24 wherein said chuck members are attached to the distal end of said collet members with hinge means permitting their radially inward deflection.

26. The connector of claim 25 wherein said chuck members are integral with said chuck members and said hinge means comprises an integral web between said chuck members and said collet members with a thickness reduced sufficiently to permit flexing.

27. The tubing connector of claim 26 wherein four four chuck members are provided at 90 degree angular spacings.

* * * * *